US012569665B2

(12) United States Patent
　　Hutzenlaub

(10) Patent No.: US 12,569,665 B2
(45) Date of Patent: Mar. 10, 2026

(54) EXTRACORPOREAL BLOOD PUMP, HEART-LUNG MACHINE, METHOD FOR OPERATING AN EXTRACORPOREAL BLOOD PUMP, AND METHOD FOR OPERATING A HEART-LUNG MACHINE

(71) Applicant: Hemovent GmbH, Aachen (DE)

(72) Inventor: Jens Hutzenlaub, Aachen (DE)

(73) Assignee: Hemovent GmbH, Aachen (DE)

( * ) Notice: Subject to any disclaimer, the term of this patent is extended or adjusted under 35 U.S.C. 154(b) by 1772 days.

(21) Appl. No.: 16/482,575

(22) PCT Filed: Nov. 8, 2017

(86) PCT No.: PCT/DE2017/000376
　　§ 371 (c)(1),
　　(2) Date: Jul. 31, 2019

(87) PCT Pub. No.: WO2018/141316
　　PCT Pub. Date: Aug. 9, 2018

(65) Prior Publication Data
　　US 2020/0038564 A1　　Feb. 6, 2020

(30) Foreign Application Priority Data

Jan. 31, 2017　(DE) ..................... 10 2017 000 843.4

(51) Int. Cl.
　　*A61M 60/113*　　(2021.01)
　　*A61M 1/16*　　(2006.01)
　　(Continued)

(52) U.S. Cl.
　　CPC ........ *A61M 60/113* (2021.01); *A61M 1/1698* (2013.01); *A61M 1/267* (2014.02);
　　(Continued)

(58) Field of Classification Search
　　CPC .. A61M 1/1698; A61M 1/267; A61M 1/3666; A61M 2205/0288; A61M 60/851;
　　(Continued)

(56) References Cited

U.S. PATENT DOCUMENTS 3,838,946 A * 10/1974 Schall ..................... F01L 15/08
　　　　　　　　　　　　417/393
3,842,440 A 　 10/1974 Karlson
　　　　　　　　(Continued)

FOREIGN PATENT DOCUMENTS

DE 　 3342534 A1 　 10/1984
DE 　 3876169 T2 　 5/1993
　　　　　(Continued)

OTHER PUBLICATIONS

International Search Report for PCT/DE2017/000376 on Aug. 9, 2018.
　　　　　　(Continued)

*Primary Examiner* — Philip R Wiest
(74) *Attorney, Agent, or Firm* — Michael J. Brown

(57)　　　　ABSTRACT

The present invention relates to a pulsatile positive-displacement pump with a flexible positive-displacement diaphragm which is operated pneumatically and by whose movement the blood is aspirated and displaced. A mechanical switching device in the interior of a drive unit ensures an autonomous operation of the blood pump, wherein no electricity or electronics system is needed.

37 Claims, 7 Drawing Sheets

Figure 1:
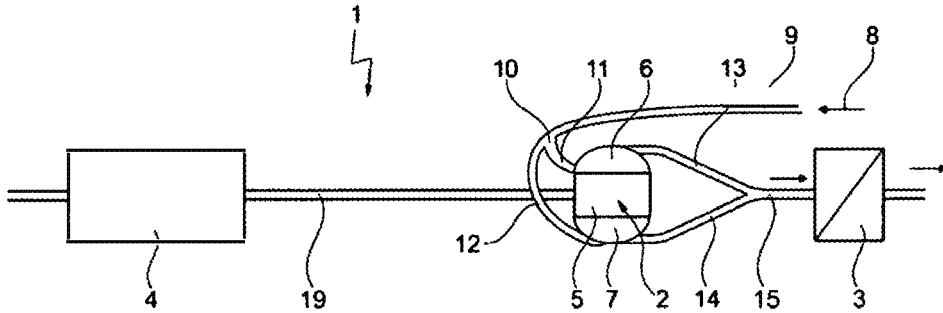

(51) Int. Cl.

| | |
|---|---|
| *A61M 1/26* | (2006.01) |
| *A61M 1/36* | (2006.01) |
| *A61M 60/268* | (2021.01) |
| *A61M 60/38* | (2021.01) |
| *A61M 60/427* | (2021.01) |
| *A61M 60/851* | (2021.01) |
| *A61M 60/892* | (2021.01) |

(52) U.S. Cl.

CPC ........ *A61M 1/3666* (2013.01); *A61M 60/268* (2021.01); *A61M 60/38* (2021.01); *A61M 60/427* (2021.01); *A61M 60/851* (2021.01); *A61M 60/892* (2021.01); *A61M 2205/0288* (2013.01)

(58) Field of Classification Search

CPC .. A61M 60/427; A61M 60/268; A61M 60/38; A61M 60/113; A61M 60/982

See application file for complete search history.

(56) References Cited

U.S. PATENT DOCUMENTS

| | | | |
|---|---|---|---|
| 3,916,449 A | 11/1975 | Davis | |
| 3,919,722 A | 11/1975 | Harmison | |
| 3,955,557 A * | 5/1976 | Takagi | A61M 60/104 |
| | | | 417/244 |
| 5,232,434 A * | 8/1993 | Inagaki | A61M 60/538 |
| | | | 623/3.28 |
| 5,269,811 A | 12/1993 | Hayes et al. | |
| 5,300,111 A * | 4/1994 | Panton | A61M 60/462 |
| | | | 623/3.19 |
| 5,314,469 A * | 5/1994 | Gao | A61M 60/894 |
| | | | 623/3.18 |
| 5,751,125 A | 5/1998 | Weiss | |
| 6,264,601 B1 | 7/2001 | Jassawalla et al. | |
| 7,981,280 B2 | 7/2011 | Carr et al. | |
| 2001/0003802 A1 | 6/2001 | Vitale | |
| 2004/0015042 A1 | 1/2004 | Vincent et al. | |
| 2004/0050789 A1* | 3/2004 | Ash | A61M 60/546 |
| | | | 210/646 |
| 2007/0158247 A1 | 7/2007 | Carr et al. | |
| 2010/0211092 A1 | 8/2010 | Forsell | |
| 2010/0234941 A1* | 9/2010 | Finocchiaro | F04B 17/04 |
| | | | 623/3.11 |
| 2013/0037485 A1 | 2/2013 | Wilt et al. | |
| 2016/0051740 A1 | 2/2016 | Wegener et al. | |
| 2019/0358375 A1* | 11/2019 | Johns | A61M 60/892 |

FOREIGN PATENT DOCUMENTS

| | | |
|---|---|---|
| DE | 69933314 T2 | 9/2007 |
| DE | 102010004600 A1 | 7/2011 |
| DE | 102011054768 A1 | 4/2013 |
| DE | 102017000843 A1 | 8/2018 |
| EP | 2517739 A2 | 10/2012 |
| EP | 2517739 B1 | 12/2013 |
| EP | 2523702 B1 | 11/2014 |
| EP | 3520833 A1 | 8/2019 |
| JP | S5012897 A | 2/1975 |
| JP | S58500793 A | 5/1983 |
| JP | H04504673 A | 8/1992 |
| JP | H0526169 A | 2/1993 |
| JP | 2004510521 A | 4/2004 |
| WO | 0230267 A2 | 4/2002 |
| WO | WO-0230267 A3 | 11/2002 |
| WO | WO-2009024308 A1 | 2/2009 |
| WO | WO-2016030917 A2 | 3/2016 |
| WO | WO-2016110613 A1 | 7/2016 |
| WO | WO-2018141316 A1 | 8/2018 |

OTHER PUBLICATIONS

International Search Report and Written Opinion for PCT/DE2017/000376 dated Mar. 1, 2018.

* cited by examiner

EXTRACORPOREAL BLOOD PUMP, HEART-LUNG MACHINE, METHOD FOR OPERATING AN EXTRACORPOREAL BLOOD PUMP, AND METHOD FOR OPERATING A HEART-LUNG MACHINE

RELATED APPLICATIONS

The present invention is a U.S. National Stage under 35 USC 371 patent application, claiming priority to Serial No. PCT/DE2017/000376, filed on 8 Nov. 2017; which claims priority of DE 10 2017 000 843.4, filed on 31 Jan. 2017, the entirety of both of which are incorporated herein by reference.

The invention relates to an extracorporeal blood pump, a heart-lung machine, a method for operating an extracorporeal blood pump and a method for operating a heart-lung machine.

The heart, as the central organ of the circulatory system, is a hollow muscle with two chambers which promotes the blood circulation by contraction and relaxation. From its left chamber (left ventricle), the blood is pumped through the arteries of the greater circulation to the capillaries of the body periphery. Through the veins, the blood reaches the right ventricle. From there, it is transported by the lung's arteries into the lung (lesser circulation) and returns to the left ventricle via the lung's veins. The lesser circulation is located in the chest.

In case of heart conditions, patients may reach a situation in which an artificial circulatory support is the only possible and therefore life-maintaining therapy.

Heart-lung machines can replace the vital circulatory functions of blood transport and gas exchange, for example during heart surgery. In derivation therefrom, heart-lung machines can also be employed for stabilizing patients with cardiac or pulmonary insufficiency over days. This process is called extracorporeal membrane oxygenation (ECMO) or extracorporeal life support (ECLS). During this process, blood is removed via cannulae which are introduced by minimally invasive methods, is then processed and returned to the patient.

WO 2009/024308 A1 discloses an electric linear drive, in particular for a pump system of an artificial heart.

EP 2 523 702 A1 discloses an assembly having a blood pump and a gas exchanger for extracorporeal membrane oxygenation.

The invention is based on the task of providing the state of the art with an improvement or an alternative.

In a first aspect of the invention, the task is solved by an extracorporeal blood pump for the aspiration and displacement of blood, the blood pump having two blood chambers and a mechanical driving unit, wherein the driving unit is arranged between the blood chambers, wherein a blood chamber has a membrane, a blood input channel and a blood output channel, wherein the blood output channels of both blood chambers are interconnected.

Some terminology will be explained in the following:

First, it is explicitly pointed out that within the framework of the present patent application, indefinite articles and numerals such as "one", "two" etc. are normally to be understood as indicating a minimum, that is, "at least one . . . ", "at least two . . . " etc., unless it becomes explicitly clear from the context or is obvious to the person skilled in the art or technically inevitable that only "exactly one . . . ", "exactly two . . . " etc. can be intended.

A "blood pump", which is frequently also called "artificial heart", is a device which assumes or supports the function of the heart and is adapted to maintain the body circulation. In particular, a blood pump can be used for support in the context of a surgery, especially for temporarily assuming the function of the heart or for supporting the heart (peri-operatively), for assuming the function of the heart or for supporting it after a surgery (post-operatively) or for other purposes, that is, not in connection with a surgery within the framework of an intervention.

An "extracorporeal blood pump" is employed outside the body.

A "blood chamber" is a component of a blood pump which is adapted to be traversed by the designated blood flow. A blood chamber is provided with a "membrane".

A "membrane" is a component of a blood pump as well as a component of a blood chamber and is adapted to alter its position and thus the volume of the blood chamber, and in doing so the designated blood stream is aspirated when the blood chamber volume is increased and the blood stream is displaced when the blood chamber volume is reduced. In particular, the "membrane" is adapted to alter its position such that a blood chamber only has approximately 10% or less of its maximum volume left, without this leading to impairments of the material behaviour of the blood chamber or of the membrane.

A "driving unit", in particular a "mechanical driving unit", is a constructive unit which drives a blood pump by transformation of energy.

A "blood input channel" is a channel through which the designated blood stream of an operating blood pump flows into an individual blood chamber.

A "blood output channel" is a channel through which the designated blood stream of an operating blood pump flows out from an individual blood chamber.

The state of the art until now has provided for predominantly employing rotary pumps for supporting the functioning of the heart or for assuming the function of the heart. However, rotary pumps can mechanically apply a relatively high level of shear stress to the blood due to their structural shape.

In the practical operation of rotary pumps, an aspiration of canulae at the input end of the rotary pump can frequently occur. The pressure/flow characteristics of rotary pumps can inherently increase the aspiration pressure and can also further increase the shear stress on the blood or even cause cavitation of the blood, whereby a damaging of blood damage can be caused.

Alternatively, membrane pumps are employed in the state of the art.

In deviation from this, a specific construction of a membrane pump is proposed which has two blood chambers and a mechanical driving unit, wherein the driving unit is arranged between the blood chambers, wherein a blood chamber has a membrane, a blood input channel and a blood output channel, wherein the blood output channels of both blood chambers are interconnected.

Specifically, among other construction varieties, it is conceivable that both blood chambers have the same nominal volume.

With a suitable design of the blood pump, undercuts and dead water zones in the area traversed by the designated blood stream will be avoided.

Advantageously, with the aspect of the invention introduced here, the blood-leading side of the blood pump can be designed such that the blood can be protected as much as possible.

In this way, it can advantageously be achieved that the forces acting on the blood are kept relatively low and all areas of the blood pump are always washed out from the blood.

Thus, advantageously, damage of the blood cells and blood clogging can be prevented.

Advantageously, in this manner, a particularly energy-efficient blood pump can be constructed which protects the blood as much as possible and which can make the designated blood stream flow back into the body through a canula.

Preferably, the blood input channels of both blood chambers are interconnected.

In a suitable embodiment, both blood input channels are interconnected in a Y-arrangement such that the designated blood stream can be distributed over both blood chambers.

Advantageously, it can be achieved in this manner that blood is collected from the body with only one canula and that the designated blood stream is pressed in the blood pump in a very gentile blood protecting manner.

Optionally, a connecting area of the blood output channels has a backflow check valve.

Some terminology will be explained in the following:

A "connecting area" is an area where the designated partial streams of the blood from both blood chambers are reconnected.

A "backflow check valve" is a component adapted to be traversed with a minor loss of pressure in one direction of the flow and with a large loss of pressure in the opposite direction of the flow. In particular, the loss of pressure in the backflow direction is so large that a backflow can be prevented. Preferably, a backflow check valve is a stop for a designated blood stream in one direction of flow whereas the designated blood stream can pass through the backflow check valve unchecked or nearly unchecked in the opposite direction of flow. It can be said that a backflow check valve exhibits the properties of an adjustable shutter which is opened or closed in dependence on the designated direction of the flow.

It is specifically conceivable, among others, that the blood output channels converge in a connecting area from both sides, similar to a Y arrangement.

Thus, with a suitable design, it is achieved that when a designated blood stream is output, backflow of the blood into the other blood chamber is prevented.

In a preferred embodiment, the backflow check valve is designed so as to be well passed by the designated blood stream on both sides, whereby the backflow check valve is washed out well by the blood.

Advantageously, it can be achieved in this manner that the blood pump has a high energy efficiency.

In addition, it can be advantageously achieved that the backflow check valve and the connecting area are washed out well by a designated blood stream, and thus the formation of thrombi can be hindered.

Furthermore, it can advantageously be achieved that during the aspiration, blood can reach the blood chamber via the blood outlet channel.

Preferably, the driving unit has a gas inlet and a gas outlet as well as a pressure chamber, wherein the pressure chamber is separated from a blood chamber by a membrane, wherein the driving unit is in operative connection to the position of the membrane.

Some terminology will be explained in the following:

A "gas inlet" is an inlet for a gaseous fluid. The gas inlet is traversed by a designated gas flow such that gas flows into the driving unit.

A "gas outlet" is an outlet for a gaseous fluid. The gas outlet is traversed by a designated gas flow such that gas flows out of the driving unit.

A "pressure chamber" is a chamber adapted to be traversed by a designated gas flow. A pressure chamber has an "effective area". The "effective area" is adapted to alter its position which can help to transform energy. In particular, an "effective area" can be a membrane separating a blood chamber from a pressure chamber.

Thus, it is concretely conceivable, for instance, to operate the blood pump with gas which releases energy into the blood stream in the driving unit.

The gas flow can be made available by a supply unit in a suitable manner.

In a suitable embodiment, a pressure chamber is arranged adjacent to a blood chamber. Thereby, the pressure chamber and the blood chamber are merely separated by the membrane.

In this way, the driving unit can be in operative connection to the position of the membrane.

In particular, by increasing the pressure in the pressure chamber, the position of the membrane can be shifted in the direction of the blood chamber.

Also, in particular, by reducing the pressure in the pressure chamber, the position of the membrane can be shifted in the direction of the pressure chamber.

In a suitable embodiment of the driving unit, the latter has an operative connection to the position of the membrane which takes into account an end-of-travel detection of the membrane.

Thus, in this suitable embodiment, the driving unit is able to detect when the membrane has reached its respective end of travel and its motion should be stopped or reversed.

Advantageously, in this manner, the driving unit can derive the energy necessary for aspirating and displacing the blood from a gas flow.

Furthermore, it can advantageously be achieved in this manner that the operative connection to the position of the membrane prevents damage of the membrane, makes it possible to aspirate and displace the blood with high energy efficiency and to maximize protection of the blood in the blood pump during processing.

Advantageously, in this manner, an adhesion of the canulae to the blood vessels, which is a frequently encountered problem in the use of blood pumps, can be prevented, since due to the pneumatically operated driving unit, the disclosed system is provided with an aspiration limit defined by a relationship between the pressure of the operating gas, the pressure at the outlet end and the aspiration pressure at the inlet end. In this manner, the complex alarm and safety units of conventional systems can be done without, thanks to the use of pressure sensors.

Optionally, the driving unit has two pressure chambers, with each pressure chamber bordering on a blood chamber with a membrane placed in between.

In a preferred embodiment, a designated blood stream in ejected in a blood chamber, while being aspirated at the other end.

With suitable design of the blood pump, the gas flow will apply pressure alternatively on a respective membrane.

Thus, it is specifically conceivable, for instance, that after a working cycle has been completed and/or an end of travel of the membrane has been reached, the gas pressure in one pressure chamber is reduced and gas pressure is applied in the other pressure chamber such that both membranes now move in opposite directions.

Advantageously, in this manner, the blood pump can be operated at a constant gas flow which makes an external circuit unnecessary.

Furthermore, it can advantageously be achieved that only one pressure level is required for a designated gas flow.

In a second aspect of the invention, the task is solved by an extracorporeal blood pump for the aspiration and displacement of blood, wherein the blood pump has one blood chamber and a mechanical driving unit, wherein the driving unit borders on the blood chamber, wherein the blood chamber has a membrane, a blood inlet channel and a blood outlet channel, wherein the driving unit has a gas inlet, a gas outlet and two pressure chambers, wherein each pressure chamber has an effective area; in particular, an effective area is a membrane, with a blood chamber being separated from a pressure chamber by a membrane, wherein the driving unit is in operative connection to the position of the membrane.

The state of the art until now has provided for predominantly employing rotary pumps for supporting the functioning of the heart or for assuming the function of the heart. However, rotary pumps can mechanically apply a relatively high level of shear stress to the blood due to their structural shape.

Alternatively, membrane pumps are used in the state of the art.

In deviation from this, a specific construction of a membrane pump is proposed, having a blood chamber and a driving unit, wherein the driving unit is provided with two pressure chambers. A pressure chamber is connected to the blood chamber via the membrane. The other pressure chamber is positioned laterally near the first pressure chamber.

In a suitable embodiment, the blood pump allows cyclic aspiration and displacement of blood with the blood chamber, wherein the driving unit can be operated according to the first aspect of the invention.

In a suitable embodiment, the second pressure chamber has an effective area which is of a different type than the membrane according to the first aspect.

Advantageously, in this manner, the blood pump with one blood chamber can be operated so as to maximize protection of the blood and so that the driving unit can obtain the required energy for aspirating and displacing the blood from a gas flow.

In addition, advantageously it can be achieved that the operative connection to the position of the membrane prevents damage to the membrane, makes it possible to aspirate and displace the blood with optimum energy efficiency and contributes to an as high as possible gentile blood protecting handling of the blood in the blood pump.

Advantageously, in this manner, it can also be achieved that an aspiration of the canulae to the blood vessels, which is a frequently encountered problem in the use of blood pumps, can be prevented, since due to the pneumatically operated driving unit, the disclosed system is provided with an aspiration limit defined by a relationship between the pressure of the operating gas, the pressure at the outlet end and the aspiration pressure at the inlet end. In this manner, the complex alarm and safety units of conventional systems can be done without, thanks to the use of pressure sensors.

Advantageously, it can also be achieved in this manner that the blood pump can be operated at a constant gas flow which makes an external circuit unnecessary.

Furthermore, it can advantageously be achieved that only one pressure level is required for a designated gas flow.

Preferably, a blood chamber has a rotationally symmetrical portion.

Advantageously, in this manner, the forces applied on the designated blood stream by the geometry of the blood chamber can reach a homogeneous level which is as low as possible.

In addition, in this manner, the flow field inside a blood chamber can be designed so to be as blood protective as possible.

Advantageously, it can also be achieved in this manner that the blood pump has a high energetic efficiency.

Optionally, a blood inlet channel and a blood outlet channel are arranged mainly in the circumferential direction at the rotationally symmetrical portion of a blood chamber.

Thus, advantageously it can be achieved that the forces acting on the blood can be minimized and all areas of the blood pump can always be washed out from the blood.

Thus, advantageously, damage of the blood cells and blood clogging can be prevented.

Advantageously, in this manner, a particularly energy-efficient blood pump can be constructed which is protective to the blood as much as possible.

Preferably, a blood inlet channel has a backflow check valve.

In an advantageous embodiment, the blood inlet channel has a backflow check valve adapted to prevent a flow of the blood against the designated direction of blood flow.

Especially preferably, the backflow check valve is designed such that it can be washed out particularly well by the designated blood stream.

Advantageously, it can be achieved in this manner that in case of displacement in a blood chamber, blood flows through the blood inlet channel.

In addition, the formation of thrombi at the backflow check valve can advantageously be prevented.

Furthermore, advantageously, a high energy efficiency of the blood pump can be achieved in this manner.

Optionally, the driving unit has a gas inlet valve and a gas outlet valve as well as a switching device, the gas inlet valve and the gas outlet valve having a closed position and an opened position with respect to a gas flow path, with the switching device having two switching end states; in particular, the switching device has exactly two switching states.

Some terminology will be explained in the following:

A "gas inlet valve" is a component for blocking or controlling the flow of gas. In the gas inlet valve, a closure part is moved, reducing or interrupting the flow. In particular, the gas inlet valve is adapted to let gas flow into the pressure chamber.

A "gas outlet valve" is also a component for blocking or controlling the flow of gas. In the gas outlet valve, a closure part is moved, reducing or interrupting the flow. In particular, the gas outlet valve is adapted to let gas flow out of the pressure chamber.

A "switching device" is a mechanical component which can cause a different switching state. Briefly before the membrane end position is reached, the switching device switches the gas inlet valve and the gas outlet valve, which causes the respective other pressure chamber to be pressurized.

As "bistability" the property of a system is understood which allows it to assume one of two possible stabile states, but to change from one state to the other only due to an exterior influence. These systems are called "bistable systems".

A "membrane end position" or "effective area end position" designates the point of reversal of a membrane position or of an effective area position.

In particular, the switching device is bistable and can therefore assume only discrete end positions.

A "gas flow path" is a path taken by a designated gas flow.

A "closed position" is the position of a valve, in particular of a gas inlet valve and/or a gas outlet valve, in which a flow of gas is prevented.

An "open position" is the position of a valve, in particular of a gas inlet valve and/or a gas outlet valve, in which a flow of gas is possible.

A "switching end state" is a stable switching state reached after a switching process of a bistable switching system has been completed.

In a particularly preferred embodiment, the switching device is designed such that the switching device switches between the two possible switching end states when a membrane end position has been reached, and thus by actuating the switching device the valve positions are moved into the respective different switching end state, whereby, when the switching end state is reached, the gas pressure in the pressure chamber is reduced and the other pressure chamber becomes pressurized, so that the two membranes or the effective surfaces move in opposite directions.

Thus, in a suitable embodiment, the membrane end position can in particular be reached if a blood chamber only has approximately 10% or less of its maximum volume left.

Thus, by changing the pressurized pressure chamber by means of switching the switching device, the connected effective surfaces and/or membranes can be moved in the opposite direction after a working cycle.

Advantageously, in this manner, a blood pump can be provided which works autonomously mechanically without having to rely on an electronics system or on exterior influences.

Furthermore, an impairment of the material behaviour of the blood chamber or of the membrane can advantageously be prevented.

Advantageously, in this manner, the blood pump can be operated at a constant gas flow which makes an external circuit unnecessary.

Preferably, in a switching end state for a blood chamber, the gas inlet valve is in the open position and the gas outlet valve in the closed position, or the gas inlet valve is in the closed position and the gas outlet valve in the open position.

Advantageously, in this manner, one pressure chamber can be filled with gas and the other pressure chamber can be gas evacuated.

Advantageously, in this manner, a blood pump can be provided which works autonomously mechanically without having to rely on an electronics system or on exterior influences, and the blood pump can be operated at a constant gas flow which makes an external circuit unnecessary.

Furthermore, the blood pump can advantageously achieve a high degree of energy efficiency.

Optionally, the switching device has a magnet.

Thus, inter alia, an arrangement of magnets is possible where a pair of magnets exhibits the maximum repelling power in the central position, resulting in a bistable switching device.

Advantageously, in this manner, a bistable and mechanically autonomous blood pump with a high energy efficiency can be achieved.

Preferably, the switching device has a lever gear.

Some terminology will be explained in the following:

A "lever gear" is a gear formed by rods, the rods predominantly forming a kinematic chain.

Advantageously, in this manner, a bistable and mechanically autonomous blood pump with high energy efficiency factor can be achieved.

Optionally, the switching device has a link with a spring-loaded roller.

Some terminology will be explained in the following:

A "slotted link" is a gear element with a slot, a web or a groove. In or on the link, there is a sliding block which is guided on both sides and to which the movement of the link is transferred.

A "spring-loaded roller" is a roller whose motion is influenced by the force of a spring.

Advantageously, in this manner, a bistable and mechanically autonomous blood pump with a high energy efficiency can be achieved.

Preferably, an area between the membranes or an area between a membrane and an effective surface has a coupling rod. In particular, the coupling rod is connected to the effective surfaces; in particular the coupling rod is connected to a membrane and to another effective surface.

Some terminology will be explained in the following:

A "coupling rod" is a component adapted to mutually couple the movement of two effective surfaces or of one effective surface and one membrane or of two membranes.

In a particularly preferred embodiment, the end position of a membrane affects the control process of the blood pump; in particular, the position of the membrane has an influence on the position of the coupling rod, and when a membrane reaches its end position, the coupling rod switches the switching device, such that the valve positions are changed to the respective other switching end state, reducing the gas pressure in the pressure chamber when a membrane end position is reached and pressurizing the other pressure chamber, such that the two membranes or effective surfaces now move in opposite directions.

Thus, in a suitable embodiment, the membrane end position can in particular be reached when a blood chamber only has approximately 10% or less of its maximum volume left.

Thus, by switching the switching device and changing the pressurized pressure chamber, the connected effective surfaces and/or membranes can be moved in the opposite direction after a working cycle.

Advantageously, in this manner, the blood pump can be operated at a constant gas flow which makes an external circuit unnecessary.

Optionally, the coupling rod has a hollow space on the inside.

Advantageously, it can be achieved in this manner that under certain circumstances, the coupling rod can have a gas flow on the inside. Thus, a hollow coupling rod can achieve part of a bypass.

Preferably, the coupling rod has a first component and a second component which are interconnected by a spring.

Advantageously, in this manner it can be achieved, that the distance between the components of the coupling rod can change when a force is reached which is defined by the spring. Thus, the effective surfaces of the pressure chambers do not have to move synchronously.

Thus, when a pressure ratio between the pressure chambers, defined by the spring, is exceeded, a movement of the effective surfaces which is otherwise coupled by the coupling rod can be uncoupled.

Optionally, the coupling rod has a valve adapted to let a designated gas stream flow through the hollow space in the coupling rod, further through the valve in the coupling rod and out from a pressure chamber via a bypass.

Some terminology will be explained in the following:

A "valve" is a component for blocking or controlling the flow of fluids. In valves, a closure component is moved in order to reduce or interrupt the flow.

A "bypass" is a flow channel through which a designated gas stream can flow. In particular, the bypass allows gas to flow out of a pressure chamber without having to pass through the gas outlet valve. Thus, the bypass is an alternative channel for letting gas in a pressure chamber flow out.

In a suitable embodiment, the valve is opened passively when a pressure ratio between the two pressure chambers is reached, which lets gas flow out of the pressurized pressure chamber via the bypass.

In an advantageous embodiment, the components of the coupling rod are connected by a spring. If the pressure ratio inside the pressure chambers exceeds a value defined by the prestress of a spring inside the coupling rod, the valve opens and gas can flow out of the pressurized pressure chamber via the bypass.

Preferably, in this manner, an additional protective device for aspiration limitation can be provided.

Preferably, the bypass has a closure device.

Some terminology will be explained in the following:

A "closure device" has a mechanical closure element adapted to release a path, block a path or throttle a flow in the path; in particular, to partially block the path. In particular, a closure device is adapted to open a bypass, close a bypass or throttle a bypass; in particular, to partially close a bypass.

Advantageously, in this manner, the valve of the coupling rod can be closed by operation of a closure device. In this way, the function of the valve can be deactivated.

It is explicitly pointed out that the subject matter of the second aspect can advantageously be combined with the subject matter of the first aspect of the invention.

In a third aspect of the invention, the task is solved by a heart-lung machine for the transport and processing of blood, wherein the heart-lung machine has a blood inlet and a blood outlet, and wherein the heart-lung machine has a blood pump according to one of the preceding Claims.

It is understood that the advantages of a blood pump for the aspiration and displacement of blood according to a first or second aspect of the invention as described above directly extend to a heart-lung machine for the transport and processing of blood.

Preferably, the heart-lung machine has an oxygenator.

Some terminology will be explained in the following:

An "oxygenator" is a product of medical technology which enriches blood with oxygen and removes carbon dioxide from the blood. An oxygenator is used for gas exchange in the blood.

Advantageously, the function of the lung can be substituted in this manner.

Optionally, the heart-lung machine has a dialyzer.

Some terminology will be explained in the following:

A "dialyzer" is a product of medical technology which is adapted to achieve an exchange of substances in the blood.

Advantageously, the function of the kidney can be substituted in this manner.

Preferably, the heart-lung machine has a filter.

Some terminology will be explained in the following:

A "filter" is a product of medical technology which is adapted to retain particles from the blood.

Advantageously, the blood can be cleaned from undesired particles in this manner.

Optionally, the heart-lung machine has a gas supply, in particular an oxygen supply.

Some terminology will be explained in the following:

A "gas supply" is an assembly which is adapted to provide for a gas flow.

Advantageously, in this manner, a heart-lung machine can be continuously supplied with oxygen and energy.

It is explicitly pointed out that the subject matter of the third aspect can advantageously be combined with the subject matter of the above aspects of the invention, both individually and cumulatively in any combination.

In a fourth aspect of the invention, the task is solved by a method of operating an extracorporeal blood pump according to a first and/or a second aspect of the invention, where the blood is collected from a patient, supplied to the blood pump by a blood inlet and supplied back to the patient by a blood outlet of the blood pump.

Some terminology will be explained in the following:

A "blood inlet" is a connection between the patient and the blood pump assembly which is adapted to be traversed by blood.

A "blood outlet" is a component through which a designated blood flow leaves the blood pump assembly and which is adapted to be traversed by blood.

Advantageously, in this manner, the blood pump can be operated with a designated blood flow from the patient and the blood can flow from the blood pump back into the patient such that the blood pump can partially or completely take over the function of the heart.

The blood is preferably aspirated in a first method step by the motion of the membrane in the blood pump and by opening of a backflow check valve in the blood inlet channel, wherein the blood flows into the blood chamber through the blood inlet channel, the backflow check valve at the blood inlet channel of the blood chamber closing in a second method step, and the blood being displaced from the blood chamber in a third method step by the movement of the membrane, wherein the backflow check valve at the blood inlet channel prevents or reduces a backflow of blood through the blood inlet channel and the blood flowing out from the blood pump through the blood outlet channel.

Advantageously, the blood pump can be rendered particularly energy-efficient in this manner and so that it effectively protects the blood.

In addition, it can advantageously be achieved that all areas traversed by a designated blood stream are washed out particularly well to prevent thrombi from forming in the blood pump.

Optionally, the blood is alternately aspirated and displaced by two blood chambers, with one blood chamber at a time aspirating and the other one displacing the blood, wherein the backflow check valve in the connecting area of the blood outlet channels prevents or reduces a backflow of blood through a blood outlet channel into a blood chamber.

Advantageously, in this manner, a pulsatile aspiration and displacement of blood can take place, the blood pump being operated with a constant gas flow which makes an external circuit unnecessary.

Advantageously, the blood pump can be rendered particularly energy-efficient in this manner and so that it effectively protects the blood.

In addition, it can advantageously be achieved that all areas traversed by a designated blood stream are washed out particularly well to prevent thrombi from forming in the blood pump.

Preferably, the movement of the coupling rod acts on the membrane and influences a movement thereof.

Advantageously, it can be achieved in this manner that a pressure chamber always has to be supplied with overpressure, but never with low pressure. The pressure chamber currently pressurized with overpressure determines the movement and entrains the membrane or the effective surface of the opposite pressure chamber so that no low pressure has to be applied here for letting the gas flow out.

This coupling can advantageously allow the blood pump to be operated with a constant gas flow which makes an external circuit unnecessary.

Optionally, the driving unit is operated with gas, the gas flowing into the driving unit through a gas inlet and out of the driving unit through a gas outlet, with a differential pressure between the blood chamber and the pressure chamber acting on the membrane and influencing a movement of the membrane.

Advantageously, the energy supply of the blood pump can thus be ensured by a gas flow, which allows construction of a particularly simple and robust blood pump.

Preferably, the gas flows into the driving unit through a gas inlet and further through an open gas inlet valve into a pressure chamber, with the gas outlet valve of this pressure chamber being closed so that the pressure in the pressure chamber increases and influences the movement of the membrane, which moves in the direction of the blood chamber either directly or with time delay.

Advantageously, in this manner it can be achieved that the pressure chamber which displaces a membrane and thus also the blood stream in the adjacent blood chamber can be operated with gas pressure; that is, it obtains energy from the pressure of the supplied gas.

Optionally, the gas flows out of a pressure chamber through a gas outlet valve and further out of the driving unit through a gas outlet, with the gas inlet valve of this pressure chamber being closed so that the pressure in the pressure chamber is reduced and influences the movement of the membrane, which moves in the direction of the pressure chamber either directly or with time delay.

Advantageously, it can be achieved in this manner that the gas used for operating the driving unit can return from the blood pump.

Preferably, the gas first flows into a first pressure chamber while gas flows out of a second pressure chamber, and when the membrane or the effective surface reaches its end position, the switching device switches the gas outlet valve so that in the next operation gas flows into the second pressure chamber while gas flows out of the first pressure chamber.

Advantageously, in this manner, a pulsatile aspiration and displacement of blood can take place, wherein the blood pump is operated with a constant gas flow which makes an external circuit unnecessary.

Optionally the switching device is switched into bistable switching states, so that after a switching operation only one pressure chamber has a gas connection with the gas inlet and the other pressure chamber has a gas connection with the gas outlet.

Advantageously, it can be achieved in this manner that the blood pump cannot get stuck between the designated switching states, which would impair the function of the blood pump or even cause its failure. The blood pump works mechanically in an autonomous manner with bistable switching states and is not dependent on an external controller, which advantageously helps to achieve a particularly safe and robust behaviour of a blood pump.

In case that an amount of differential pressure between the pressure chambers is exceeded, the gas preferably flows out of a pressure chamber via the valve.

Advantageously, in this manner it can be achieved that an additional protective device for aspiration limitation is provided, reducing the risks in using a blood pump.

Optionally, the closure part closes the bypass so that no gas, or only a reduced flow of gas, can exit from the valve.

Advantageously, in this manner, the protective function enabled with the bypass and the associated valve can be deactivated in order to promote a higher pump performance.

It is explicitly pointed out that the subject matter of the fourth aspect can advantageously be combined with the subject matter of the above aspects of the invention, both individually and cumulatively in any combination.

In a fifth aspect of the invention, the task is solved by a method of operating a heart-lung machine according to the third aspect of the invention, where the blood is collected from a patient, supplied to the heart-lung machine and supplied back to the patient by the heart-lung machine.

Advantageously, in this manner, the heart-lung machine can be operated with a designated blood stream from the patient and the blood can flow from the blood pump back into the patient so that the heart-lung machine can partially or entirely substitute the function of the heart and of the lung.

Preferably, the blood pump of the heart-lung machine is operated by means of a method according to the fourth aspect of the invention.

Advantageously, in this manner, the advantages of a method of operating a blood pump according to a fourth aspect of the invention as described above can directly extend to a method of operating a heart-lung machine.

Optionally, the blood is supplied to the blood pump and subsequently to the oxygenator and/or the filter and/or the dialyzer.

Advantageously, in this manner it can be achieved that the blood collected from the patient can be oxygenated, cleaned from carbon dioxide and undesired particles, and an exchange of substances can take place in the blood. Thus, the functions of the heart, the lung and the kidneys can be substituted completely or partially.

It is explicitly pointed out that the subject matter of the fifth aspect can advantageously be combined with the subject matter of the above aspects of the invention, both individually and cumulatively in any combination.

Figure 2:
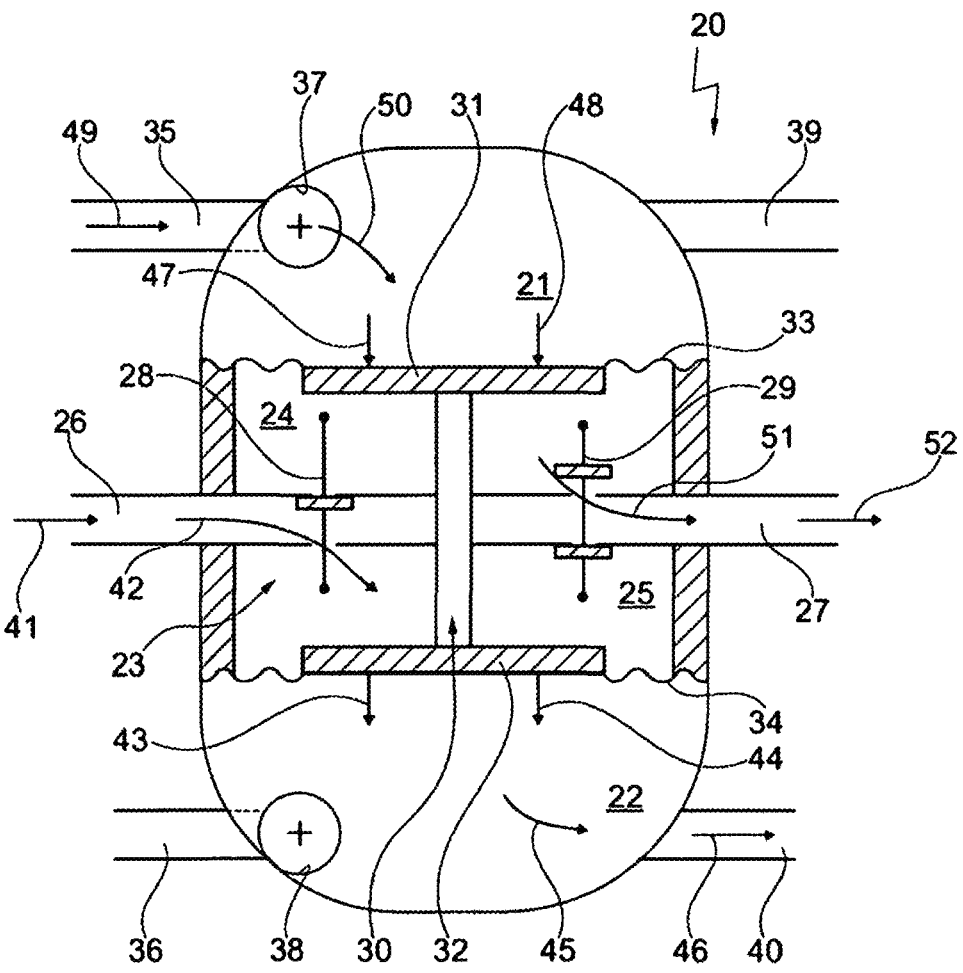
Figure 3:
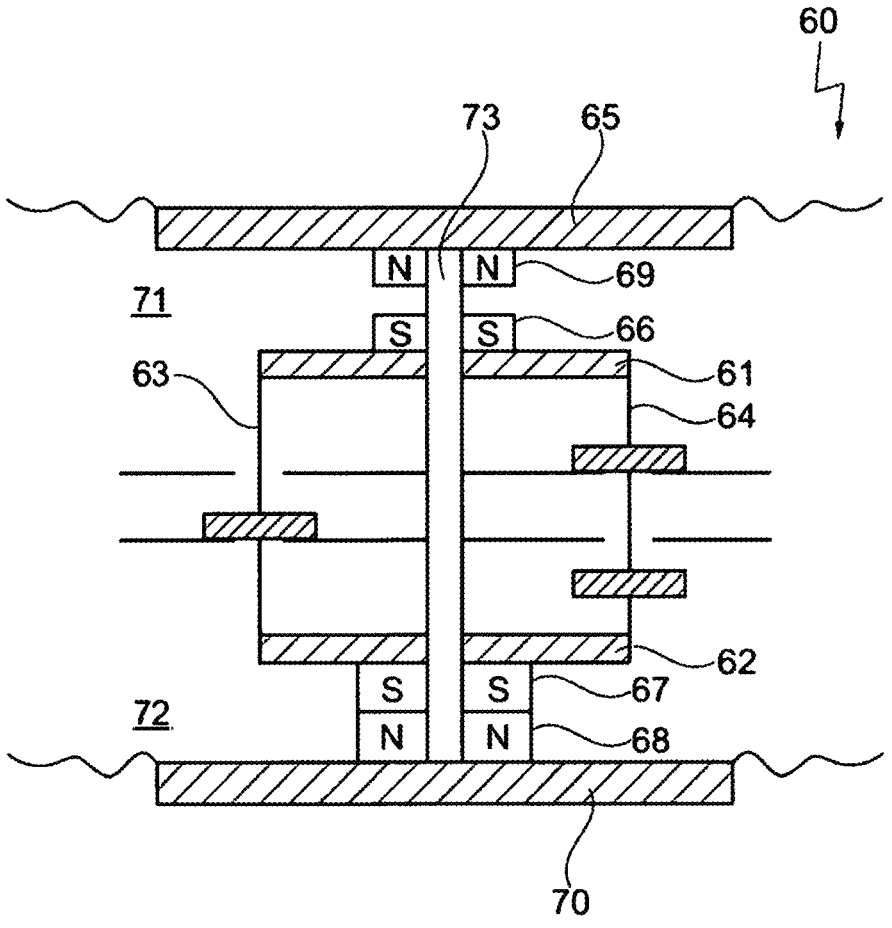
Figure 4:
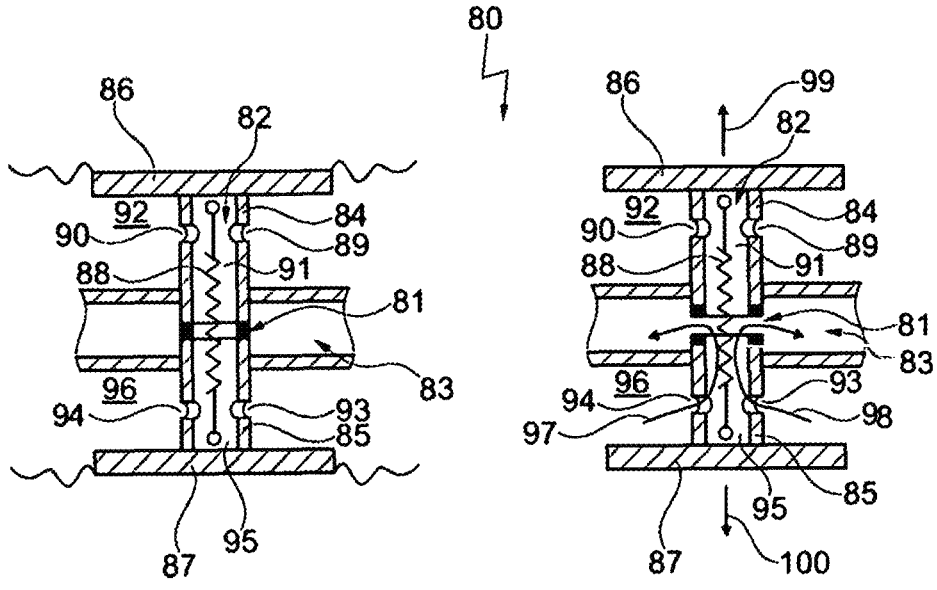
Figure 5:
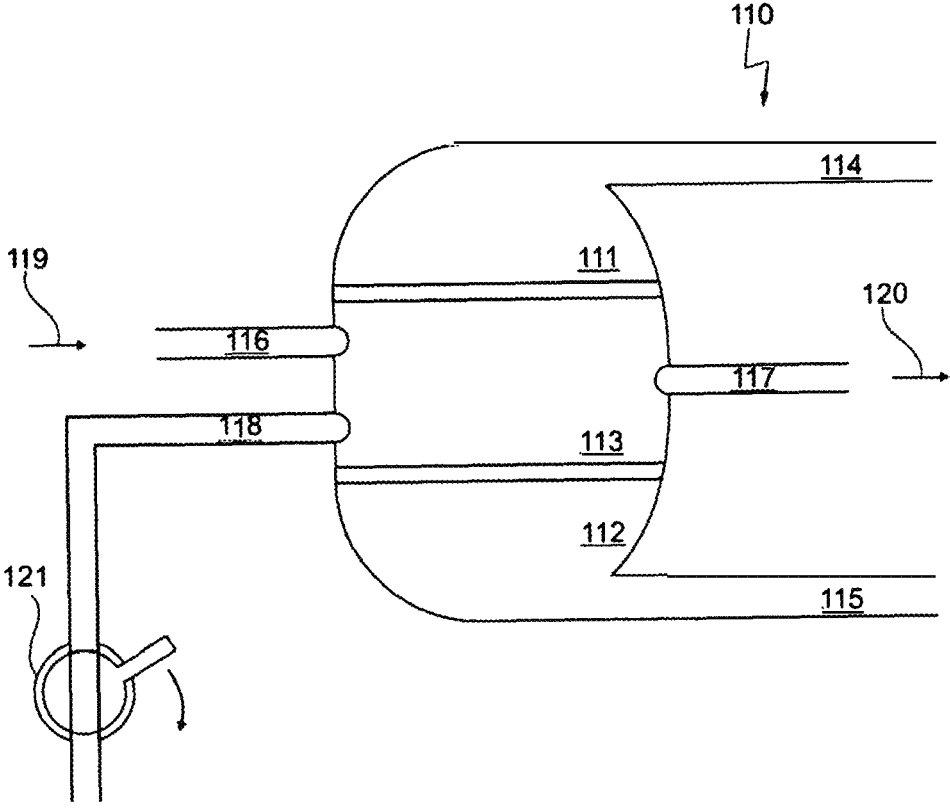
Figure 6:
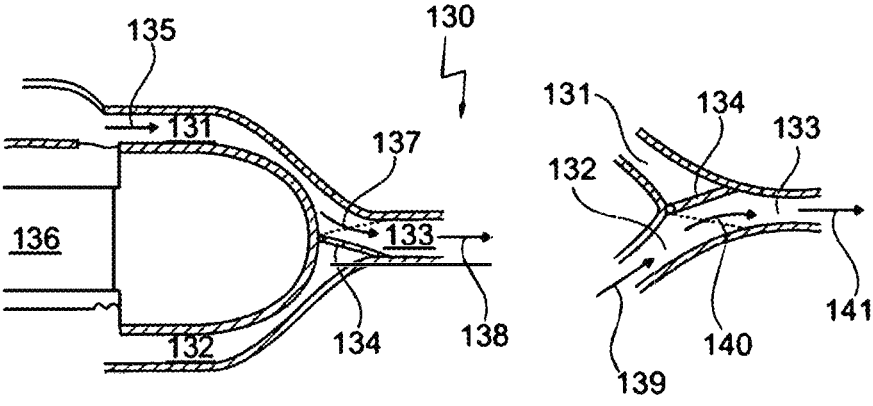
Figure 7:
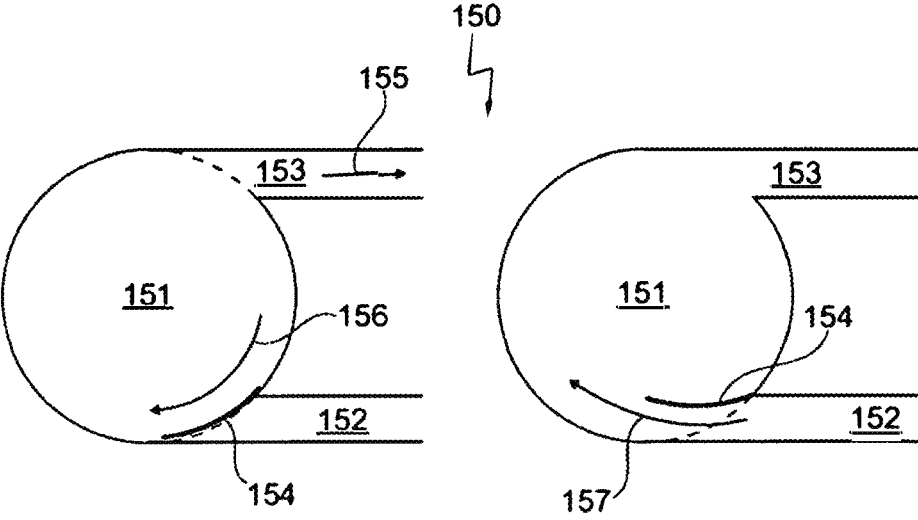

In the following, the invention will be explained in more detail by means of examples of embodiment with reference to the drawings wherein FIG. 1 schematically shows a heart-lung machine, FIG. 2 schematically shows a blood pump, FIG. 3 schematically shows a switching device, FIG. 4 schematically shows an embodiment of a coupling rod assembly with valve and bypass, FIG. 5 schematically shows a blood pump with bypass and closure part, FIG. 6 schematically shows a connecting portion of the blood outlet channels and FIG. 7 schematically shows a blood chamber unit with blood inlet channel, blood outlet channel and backflow check valve.

Figure 8:
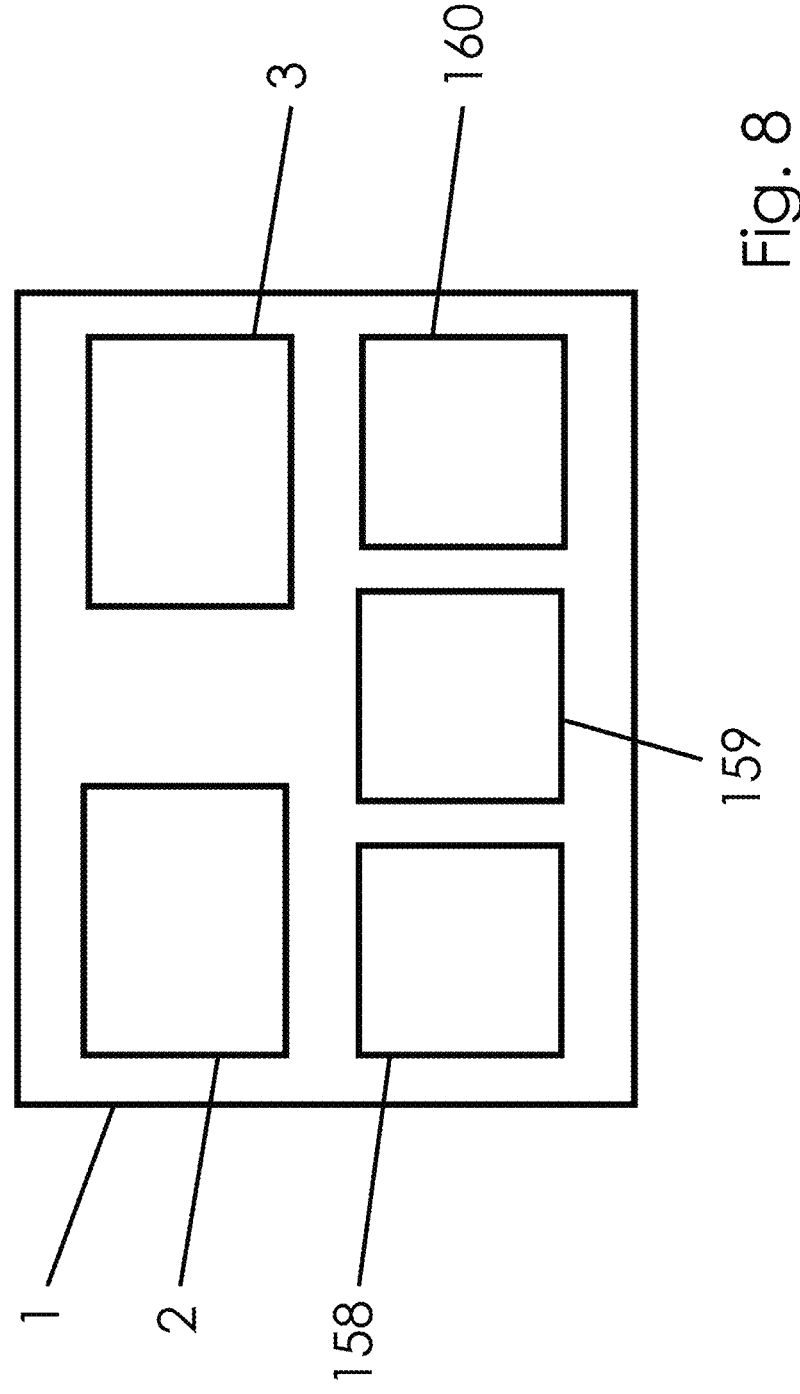

FIG. 8 is a block diagram showing a heart lung machine comprising a blood pump, oxygenator, dialyzer, filter and gas supply.

The heart-lung machine 1 in FIG. 1 substantially consists of a blood pump 2, an oxygenator 3 and a supply unit 4.

The blood pump 2 substantially consists of a driving unit 5 and two blood chambers 6, 7.

A designated blood stream (not shown) flows in a designated blood stream inlet direction 8 in a blood inlet 9 from the patient (not shown) in the direction of the blood pump 2.

Before the designated blood stream (not shown) reaches the blood pump 2, it is divided in a flow splitter 10 and flows, downstream of the flow splitter 10, into two blood inlet channels 11, 12 into a respective blood chamber 6, 7, is pressurized therein by the driving unit 5, and leaves the blood pump 2 via a respective blood outlet channel 13, 14.

At the end of the blood outlet channels 13, 14, the designated blood streams (not shown) reconverge in a connecting area 14, and from there, the blood stream flows on downstream in the direction of the oxygenator 3.

The designated blood stream enters the oxygenator in the blood flow direction 16 and exits the oxygenator 3 in the blood flow direction 17.

Downstream of the oxygenator 3, the designated blood stream (not shown) flows back to the patient (not shown) through a blood outlet 18.

The supply unit 4 supplies the blood pump 2, in particular the driving unit 5 of the blood pump 2, with a gas flow (not shown) via a gas inlet 19 and thus supplies the blood pump 2 with the energy required for pumping the designated blood stream (not shown).

The blood pump 20 in FIG. 2 substantially consists of two blood chambers 21, 22 and a driving unit 23.

The driving unit 23 substantially consists of two pressure chambers 24, 25, a gas inlet 26, a gas outlet 27, a gas inlet valve 28, a gas outlet valve 29 and a coupling rod 30.

The coupling rod 30 has one effective surface 31, 32 each at its ends.

The blood chamber 21 is separated from the pressure chamber 24 by the effective surface 31 and the membrane 33 so that a fluid (not shown) can neither flow from the blood chamber 21 into the pressure chamber 24 nor from the pressure chamber 24 into the blood chamber 21.

The blood chamber 22 is separated from the pressure chamber 25 by the effective surface 32 and the membrane 34 so that a fluid (not shown) can neither flow from the blood chamber 22 into the pressure chamber 25 nor from the pressure chamber 25 into the blood chamber 22.

The gas inlet valve 28 can be switched such that a designated gas flow (not shown) can flow via the gas inlet 26 into the pressure chamber 24 or the pressure chamber 25.

The gas inlet valve 29 can be switched such that a designated gas flow (not shown) can flow from the pressure chamber 24 or the pressure chamber 25 into the gas outlet 27.

A designated blood stream (not shown) flows through a blood inlet channel 35 and a backflow check valve 37 into the blood chamber 21 and from there downstream via the blood outlet channel 39 and out of the blood chamber 21.

A designated blood stream (not shown) flows through a blood inlet channel 36 and a backflow check valve 38 into the blood chamber 22 and from there downstream via the blood outlet channel 40 and out of the blood chamber 22.

The blood pump 20 in FIG. 2 can for example be in the following state: a designated gas flow (not shown) moves through the gas inlet 26 into the driving unit 23 in a gas inlet direction 41. There the designated gas flow (not shown) moves into the pressure chamber 25 in the gas flow direction 42 via the gas inlet valve 28. Since the gas outlet valve 29 closes the pressure chamber 25, the gas pressure in the pressure chamber 25 increases.

The gas pressure in the pressure chamber 25 acts on the effective surface 32 and on the membrane 34 and becomes so high that the effective surface 32 and the membrane 34 move in the direction of the blood chamber 22 with the direction 43, 44 of movement.

In this way, the volume of the blood chamber 22 is reduced, the backflow check valve 38 is closed and a designated blood stream (not shown) flows toward the blood outlet channel 40 in a blood flow direction 45 and further on through the blood outlet channel 40 and out of the blood pump 20 in the blood flow direction 46.

The direction 43, 44 of movement of the effective surface 32 is transferred via the coupling rod 30 to the direction 47, 48 of movement of the effective surface 31 so that the effective surface 31 and the membrane 33 move in such a way that the volume of the blood chamber 21 increases.

In this way, a designated blood stream (not shown) is aspirated through the blood inlet channel 35 in the blood inlet direction 49 and further downstream in the blood flow direction 50 into the blood chamber 21, through the backflow check valve 37 which opens in this manner.

At the same time, the direction 47, 48 of movement of the effective surface 31 and of the membrane 33 leads to a reduction in the volume of the pressure chamber 24, causing a designated gas flow (not shown) to flow in the gas flow direction 51 through the open gas outlet valve 29 out of the pressure chamber 24 into the gas outlet 27 and to leave the driving unit 23 in the gas outlet direction 52 further downstream.

The switching device 60 in FIG. 3 substantially consists of an upper switching component 61, a lower switching component 62 and of the magnets 66, 67, 68, 69.

The upper switching component 61 and the lower switching component 62 each connect the gas inlet valve 63 and the gas outlet valve 64 at the upper and the lower end of the gas inlet valve 63 and the gas outlet valve 64.

The positions of the gas inlet valve 63 and the gas outlet valve 64 determine into which, or out of which, of the pressure chambers 71, a designated gas flow (not shown) flows; the positions are switched by the switching device 60.

The pressure chamber 71 contains the magnets 66, 69 with opposite polarization. The magnet 66 is connected to the upper switching component 61. The magnet 69 is connected to the effective surface 65 and therefore moves together with the effective surface 65. Since the effective surface 65 is connected to the effective surface 70 via the coupling rod 73, the coupling rod 73 and the effective surface 70 move along likewise.

The pressure chamber 72 contains the magnets 67, 68 with opposite polarization. The magnet 67 is connected to the lower switching component 62. The magnet 68 is connected to the effective surface 70 and therefore moves together with the effective surface 70. Since the effective surface 70 is connected to the effective surface 65 via the coupling rod 73, the coupling rod 73 and the effective surface 65 move along likewise.

The magnets 66, 69 and the magnets 67, 68 have respective opposite polarizations and therefore attract each other. The attraction force of the magnets 66, 69 and of the magnets 67, 68 depends on the distance between the respective pair of magnets. When the magnets 66, 69 or the magnets 67, 68 are in contact, their attraction force is strongest.

Due to the arrangement of the magnets 66, 67, 68, 69, in combination with the construction of the switching device 60 and the attraction force of the magnets 66, 67, 68, 69, a bistable embodiment of the switching device 60 is achieved in the kinematic of the blood pump 20 with the switching device 60 which has already been described in the explanation of FIG. 2, allowing for bistable switching states.

The embodiment of a coupling rod arrangement 80 with a valve and a bypass in FIG. 4 (the left partial figure shows the embodiment of the coupling rod arrangement 80 with closed valve 81, the right partial figure shows the embodiment of the coupling rod arrangement with open valve 81) substantially consists of a valve 81, a coupling rod 82 and a bypass 83.

The coupling rod 82 has an upper coupling rod component 84 and a lower coupling rod component 85. The upper coupling rod component 84 is fixedly connected with the effective surface 86. The lower coupling rod component 85 is fixedly connected with the effective surface 87.

The upper coupling rod component 84 and the lower coupling rod component 85 are pressed together by a spring 88 at the site of the valve 81. If a force is exerted on the effective surfaces 86, 87 which is larger than the spring force and acts in the direction opposite to the spring force, the valve 81 is opened (right partial figure).

The upper coupling rod component 84 is hollow on the inside and has bore holes 89, 90 which can connect the hollow space 91 of the upper coupling rod component 84 to the pressure chamber 92. The bore holes 89, 90 are arranged such that they release the hollow space 91 of the upper coupling rod component 84 with the pressure chamber 92 only if the latter has a volume of more than 50% of its nominal pressure chamber volume.

The lower coupling rod component 85 is also hollow on the inside and has bore holes 93, 94 which can connect the hollow space 95 of the lower coupling rod component 85 to the pressure chamber 96. The bore holes 93, 94 are arranged such that they release the hollow space 95 of the lower coupling rod component 85 with the pressure chamber 96 only if the latter has a volume of more than 50% of its nominal pressure chamber volume.

In particular, the coupling rod 82 is designed such that there is no state in which the bore holes 89, 90 connect the hollow space 91 of the upper coupling rod component 84 with the pressure chamber 92 while at the same time the bore holes 93, 94 connect the hollow space 95 of the lower coupling rod component 85 with the pressure chamber 96. In this manner, it is ensured that the hollow spaces 91, 95 of the coupling rod 82 do not compensate the pressure between the pressure chambers 92, 96.

If a force 99, 100 acts on the effective surfaces 86, 87 which is larger than the spring force and acts in the direction opposite to the spring force, the valve 81 opens (right partial figure). If the pressure chamber 96 has a volume of more than 50% of its nominal pressure chamber volume, a designated gas flow (not shown) moves from the pressure chamber 96 in the gas flow direction 97, 98 through the bore hole 93, 94 into the hollow space 95, through the open valve 81 and further downstream into the bypass 83.

Alternatively (not shown), a designated gas flow (not shown) moves from the pressure chamber 92 in the gas flow direction (not shown) through the bore holes 89, 90 into the hollow space 91, through the open valve 81 and further downstream into the bypass 83 if the force 99, 100 exerted on the effective surfaces 86, 87 is larger than the spring force, acts in the direction opposite to the spring force and the pressure chamber 92 has a volume of more than 50% of its nominal pressure chamber volume.

The blood pump 110 in FIG. 5 substantially consists of the blood chambers 111, 112 and of a driving unit 113.

Each of the blood chambers 111, 112 has a blood inlet channel (not shown) and a blood outlet channel 114, 115.

The driving unit 113 has a gas inlet 116, a gas outlet 117 and a bypass 118 so that a designated gas flow (not shown)

can flow through the gas inlet 116 into the driving unit 113 in the gas inlet direction 119 and can flow out through the gas outlet 117 in the gas outlet direction 120.

If the valve 81 inside the driving unit 113 is opened, a designated gas flow (not shown) can flow out of the driving unit 113 through the bypass 118.

The bypass has a closure device 121 which makes it possible to open the bypass so that a designated gas flow (not shown) can move through the bypass when the valve 81 is opened; and to close it so that a designated gas flow (not shown) cannot move through the bypass when the valve 81 is opened; or to check it so that a designated gas flow (not shown) can only move through the bypass in a checked manner when the valve 81 is open.

The connecting area 130 in FIG. 6 (the left part and the right part show alternative blood stream paths) substantially consists of the blood outlet channels 131, 132 which meet in the connecting area 130, of the blood outlet 133 to the patient (not shown) and of a backflow check valve 134.

A designated blood stream (not shown) can flow out of the blood pump 136 through the blood outlet channel 131 in the blood flow direction 135; then, further on downstream, it encounters the connecting area 130, which is traversed in the blood flow direction 137, and the backflow check valve 134 which is traversed in the blood flow direction 137 as well. Further downstream, the designated blood stream (not shown) flows from the connecting area 130 back to the patient (not shown) through the blood outlet 133 in the blood flow direction 138.

A designated blood stream (not shown) can flow out of the blood pump 136 through the blood outlet channel 132 in the blood flow direction 139; then, further on downstream, it encounters the connecting area 130, which is traversed in the blood flow direction 140, and the backflow check valve 134 which is traversed in the blood flow direction 140 as well. Further downstream, the designated blood stream (not shown) flows from the connecting area 130 back to the patient (not shown) through the blood outlet 133 in the blood flow direction 141.

The backflow check valve 134 prevents or reduces any backflow of a designated blood stream (not shown) through the blood outlet channel 131, 132 which is not connected to the respective blood displacing blood chamber (not shown) of the blood pump 136.

A blood chamber unit 150 in FIG. 7 (the left partial figure shows the displacement of blood from the blood chamber; the right partial figure shows an aspiration of blood into the blood chamber) substantially consists of a blood chamber 151, a blood inlet channel 152, a blood outlet channel 153 and a backflow check valve 154.

When a designated blood stream (not shown) is displaced, the designated blood stream (not shown) flows out of the blood chamber 151 in the blood flow direction 115 through the blood outlet channel 153. This causes a circulation 156 of the designated blood stream (not shown) in the blood chamber 151.

When a designated blood stream (not shown) is displaced from the blood chamber 153, the backflow check valve 154 prevents or reduces a flow of the blood stream (not shown) out of the blood chamber 151 through the blood inlet channel 152.

When a designated blood stream (not shown) is aspirated, the designated blood stream (not shown) flows through the blood inlet channel 152 into the blood chamber 151 in the blood flow direction 157 and through the backflow check valve 154.

LIST OF REFERENCE NUMBERS 1 heart-lung machine
2 blood pump
3 oxygenator
4 supply unit
5 driving unit
6 blood chamber
7 blood chamber
8 blood stream inlet direction
9 blood inlet
10 flow splitter
11 blood inlet channel
12 blood inlet channel
13 blood outlet channel
14 blood outlet channel
15 connecting area
16 blood flow direction
17 blood flow direction
18 blood outlet
19 gas inlet
20 blood pump
21 blood chamber
22 blood chamber
23 driving unit
24 pressure chamber
25 pressure chamber
26 gas inlet
27 gas outlet
28 gas inlet valve
29 gas outlet valve
30 coupling rod
31 effective surface
32 effective surface
33 membrane
34 membrane
35 blood inlet channel
36 blood inlet channel
37 backflow check valve
38 backflow check valve
39 blood outlet channel
40 blood outlet channel
41 gas inlet direction
42 gas flow direction
43 direction of movement
44 direction of movement
45 blood flow direction
46 blood flow direction
47 direction of movement
48 direction of movement
49 blood inlet direction
50 blood flow direction
51 gas flow direction
52 gas outlet direction
60 switching device
61 upper switching component
62 lower switching component
63 gas inlet valve
64 gas outlet valve
65 effective surface
66 magnet
67 magnet
68 magnet
69 magnet
70 effective surface
71 pressure chamber
72 pressure chamber 73 coupling rod
80 coupling rod arrangement
81 valve
82 coupling rod
83 bypass
84 upper coupling rod component
85 lower coupling rod component
86 effective surface
87 effective surface
88 spring
89 bore hole
90 bore hole
91 hollow space
92 pressure chamber
93 bore hole
94 bore hole
95 hollow space
96 pressure chamber
97 gas flow direction
98 gas flow direction
99 force
100 force
110 blood pump
111 blood chamber
112 blood chamber
113 driving unit
114 blood outlet channel
115 blood outlet channel
116 gas inlet
117 gas outlet
118 bypass
119 gas inlet direction
120 gas outlet direction
121 closure device
130 connecting area
131 blood outlet channel
132 blood outlet channel
133 blood outlet
134 backflow check valve
135 blood flow direction
136 blood pump
137 blood flow direction
138 blood flow direction
139 blood flow direction
140 blood flow direction
141 blood flow direction
150 blood chamber unit
151 blood chamber
152 blood inlet channel
153 blood outlet channel
154 backflow check valve
155 blood flow direction
156 circulation
157 blood flow direction

The invention claimed is:

1. Extracorporeal blood pump for the aspiration and displacement of blood, wherein the blood pump has two blood chambers and a mechanical driving unit, wherein the driving unit is arranged between the blood chambers, wherein each blood chamber has a membrane, a blood inlet channel for entry of designated blood into an inlet position of the blood chamber and a blood outlet channel at an outlet position of the blood chamber for exit of the designated blood out from the blood chamber, characterized in that the blood inlet channel and blood outlet channel of each blood chamber are at different positions of the blood chamber, the blood outlet channels of both blood chambers are interconnected, and wherein the driving unit has a gas inlet, a gas outlet and a pressure chamber, wherein the pressure chamber is separated from the blood chambers by the membranes of the two blood chambers, the driving unit being in operative connection with the membrane, and wherein an area between the membranes of the two blood chambers or an area between at least one of the membranes of the two blood chambers and an effective surface comprises a coupling rod.

2. Extracorporeal blood pump according to claim 1, characterized in that the blood inlet channels of both blood chambers are interconnected.

3. Extracorporeal blood pump according to claim 1, characterized in that a connecting area of the blood inlet channels has a backflow check valve.

4. Extracorporeal blood pump according to claim 1, characterized in that the driving unit has two pressure chambers, wherein each pressure chamber is bordering on one of the blood chambers via one of the membranes.

5. Extracorporeal blood pump for the aspiration and displacement of blood, wherein the blood pump has a blood chamber and a mechanical driving unit, wherein the driving unit is bordering on the blood chamber, wherein the blood chamber has a membrane, a blood inlet channel and a blood outlet channel, wherein the blood inlet channel enters the blood chamber at an inlet position and the blood outlet channel exits the blood chamber at an outlet position, and where the inlet position and outlet positions are not interconnected, wherein the driving unit has a gas inlet, a gas outlet as well as two pressure chambers, wherein each pressure chamber has an effective surface, with the blood chamber being separated from the pressure chamber via the membrane, the driving unit being in operative connection with the membrane, and wherein an area between the membrane and at least one of the effective surfaces comprises a coupling rod.

6. Extracorporeal blood pump according to claim 5, characterized in that a blood chamber has a rotationally symmetrical portion.

7. Extracorporeal blood pump according to claim 6, characterized in that the blood inlet channel and the blood outlet channel are arranged mainly in the circumferential direction on a rotationally symmetrical portion of the blood chamber.

8. Extracorporeal blood pump according to claim 1, characterized in that the blood inlet channel has a backflow check valve.

9. Extracorporeal blood pump according to claim 1, characterized in that the driving unit has a gas inlet valve and a gas outlet valve as well as a switching device, wherein the gas inlet valve and the gas outlet valve have a closed position and an opened position with respect to a gas flow path, with the switching device having two switching end states.

10. Extracorporeal blood pump according to claim 9, characterized in that in a switching end state for the blood chamber, the gas inlet valve is in the opened position and the gas outlet valve is in the closed position or the gas inlet valve is in the closed position and the gas outlet valve is in the opened position.

11. Extracorporeal blood pump according to claim 9, characterized in that the switching device has a magnet.

12. Extracorporeal blood pump according to claim 9, characterized in that the switching device has a lever gear.

13. Extracorporeal blood pump according to claim 9, characterized in that the switching device has a link with a spring-loaded roller.

14. Extracorporeal blood pump according to claim 1, wherein the coupling rod is connected to at least one of the membranes of the two blood chambers and to another effective surface.

15. Extracorporeal blood pump according to claim 14, characterized in that the coupling rod has a hollow space on the inside.

16. Extracorporeal blood pump according to claim 14, characterized in that the coupling rod has a first component and a second component, the first component and the second component being connected to a spring.

17. Extracorporeal blood pump for the aspiration and displacement of blood, wherein the blood pump has two blood chambers and a mechanical driving unit, wherein the driving unit is arranged between the blood chambers, wherein a blood chamber has a membrane, a blood inlet channel and a blood outlet channel, characterized in that the blood outlet channels of both blood chambers are interconnected, and wherein the driving unit has a gas inlet and a gas outlet and a pressure chamber, wherein the pressure chamber is separated from a blood chamber by the membrane, the driving unit being in operative connection with the position of the membrane, and wherein an area between the membranes of the two blood chambers or an area between at least one of the membranes of the two blood chambers and an effective surface comprises a coupling rod, and wherein the coupling rod has a hollow space on the inside, and wherein the coupling rod has a valve which is constructed so that a designated gas flow can move through the hollow space in the coupling rod and further on through the valve in the coupling rod and out of a pressure chamber via a bypass.

18. Extracorporeal blood pump according to claim 17, characterized in that the bypass has a closure device.

19. Heart-lung machine for the transport and processing of blood, the heart-lung machine having a blood inlet and a blood outlet, characterized in that the heart-lung machine has an extracorporeal blood pump according to claim 1.

20. Heart-lung machine according to claim 19, characterized in that the heart-lung machine has an oxygenator.

21. Heart-lung machine according to claim 19, characterized in that the heart-lung machine has a dialyzer.

22. Heart-lung machine according to claim 19, characterized in that the heart-lung machine has a filter.

23. Heart-lung machine according to claim 19, characterized in that the heart-lung machine has a gas supply, in particular an oxygen supply.

24. Method of operating an extracorporeal blood pump according to claim 1, characterized in that blood is collected from a patient, supplied to the blood pump by a blood supply and supplied back to the patient from a blood outlet of the blood pump.

25. Method according to claim 24, characterized in that in a first method step, the blood is aspirated by moving the membrane in the blood pump and by a backflow check valve in the blood inlet channel which consequently opens, wherein the blood flows into the blood chamber through the blood inlet channel, the backflow check valve at the blood inlet channel of the blood chamber closing in a second method step and the blood being displaced from the blood chamber by moving the membrane in a third method step; wherein the backflow check valve at the blood inlet channel prevents or reduces a backflow of blood through the blood inlet channel and the blood flowing out of the blood pump through the blood outlet channel.

26. Method according to claim 24, characterized in that the blood is alternately aspirated and displaced by two blood chambers; one blood chamber aspirating blood and the other blood chamber displacing blood, alternately; with the backflow check valve in the connecting area of the blood outlet channels preventing or reducing a backflow of blood into a blood chamber through a blood outlet channel.

27. Method according to claim 24, characterized in that the movement of the coupling rod acts on the membrane and influences a movement of the membrane.

28. Method according to claim 24, characterized in that the driving unit is operated with gas, wherein the gas flows into the driving unit through a gas inlet, wherein the gas flows out of the driving unit through a gas outlet; wherein a differential pressure between the blood chamber and the pressure chamber acts on the membrane and influences a movement of the membrane.

29. Method according to claim 28, characterized in that the gas flows into the driving unit through a gas inlet and subsequently into a pressure chamber through an open gas inlet valve, with the gas outlet valve of this pressure chamber being closed so that the pressure in the pressure chamber rises and influences the movement of the membrane, wherein the membrane moves in the direction of the blood chamber either directly or with time delay.

30. Method according to claim 28, characterized in that the gas flows out of a pressure chamber through a gas outlet valve and subsequently out of the driving unit through a gas outlet, with the gas inlet valve of this pressure chamber being closed so that the pressure in the pressure chamber is reduced and influences the movement of the membrane, wherein the membrane moves in the direction of the pressure chamber either directly or with time delay.

31. Method according to claim 28, characterized in that gas alternately flows into a first pressure chamber while gas flows out of a second pressure chamber and the switching device switches the gas inlet valve and the gas outlet valve when a membrane end position or an effective surface end position is reached so that subsequently, gas flows into the second pressure chamber while gas flows out of the first pressure chamber.

32. Method according to claim 31, characterized in that the switching device is switched in bistable switching states so that after a switching step, only one pressure chamber is in gas connection with the gas inlet and the other pressure chamber is in gas connection with the gas outlet.

33. Method according to claim 24, characterized in that when an amount of differential pressure between the pressure chambers is exceeded, the gas flows out of a pressure chamber via the valve.

34. Method according to claim 24, characterized in that the closure device closes the bypass so that no gas, or only a reduced flow of gas, can flow through the valve.

35. Method of operating a heart-lung machine according to claim 19, characterized in that blood is collected from a patient, is supplied to the heart-lung machine and from the heart-lung machine back to the patient.

36. Method according to claim 35, characterized in that the blood pump of the heart-lung machine is operated with a method according to one of claims 24 through 34.

37. Method according to claim 35, characterized in that the blood is supplied to the blood pump and subsequently to the oxygenator and/or the filter and/or the dialyzer.

\*   \*   \*   \*   \*